(12) United States Patent
Moyse et al.

(10) Patent No.: US 7,302,831 B2
(45) Date of Patent: Dec. 4, 2007

(54) SCRATCH TESTING DEVICE

(76) Inventors: Allan H. Moyse, 5035 Raymond Stotzer Pkwy., College Station, TX (US) 77845; Hung-Jue Su, 4605 Valleybrook, College Station, TX (US) 77845

( * ) Notice: Subject to any disclaimer, the term of this patent is extended or adjusted under 35 U.S.C. 154(b) by 0 days.

(21) Appl. No.: 11/300,798

(22) Filed: Dec. 15, 2005

(65) Prior Publication Data

US 2006/0150710 A1    Jul. 13, 2006

Related U.S. Application Data

(60) Provisional application No. 60/636,689, filed on Dec. 16, 2004.

(51) Int. Cl.
*G01N 3/46* (2006.01)

(52) U.S. Cl. .......................................... 73/81

(58) Field of Classification Search .................... 73/78, 73/81, 85, 7
See application file for complete search history.

(56) References Cited

U.S. PATENT DOCUMENTS

| | | | | |
|---|---|---|---|---|
| 2,938,377 A * | 5/1960 | Sklar | ............................. | 73/83 |
| 5,357,786 A * | 10/1994 | Lung et al. | .................... | 73/81 |
| 5,804,706 A * | 9/1998 | Williston | ....................... | 73/78 |
| 6,945,097 B2 * | 9/2005 | Jardret et al. | .................. | 73/81 |
| 7,121,136 B2 * | 10/2006 | Tsujii et al. | ................... | 73/81 |
| 7,168,291 B2 * | 1/2007 | Kuhman et al. | ................. | 73/7 |
| 2005/0172702 A1 * | 8/2005 | Gitis et al. | ....................... | 73/81 |

* cited by examiner

*Primary Examiner*—Thomas P. Noland
(74) *Attorney, Agent, or Firm*—Tod T. Tumey

(57) ABSTRACT

A device and method for scratch and/or mar testing the surface of a material specimen. In an embodiment, the scratch testing device comprises a scratching member. In addition, the scratch testing device comprises a carriage operable to move the scratching member. Further, the scratch testing device comprises a load mechanism, wherein the load mechanism applies a load to the scratching member.

20 Claims, 7 Drawing Sheets

SCRATCH TESTING DEVICE

CROSS-REFERENCE TO RELATED APPLICATIONS

This non-provisional application claims the benefit of U.S. Provisional Application No. 60/636,689, filed Dec. 16, 2004, which is hereby incorporated by reference in its entirety.

STATEMENT REGARDING FEDERALLY SPONSORED RESEARCH OR DEVELOPMENT

Not applicable.

BACKGROUND OF THE INVENTION

1. Field of the Invention

The present invention relates generally to the field of surface testing instruments, and more particularly relates to the field of surface testing instruments for performing scratch, mar, and wear-resistance testing on material samples.

2. Background of the Invention

Surface testing and analysis of materials, particularly of polymers, is becoming a rapidly expanding area of research in the field of materials science and mechanics. The surge of interest in the subject of scratch and/or mar resistance of polymers stems from the increasing use of polymers in various applications such as in hard discs, optical lenses, windshields, automotive parts, durable goods, etc.

In general, there are two basic types of material surface damage—mar and scratch. A mar is a mark caused by a sliding body that is too shallow to be perceived by the casual human eyes alone but nevertheless may become visible when present in large quantities. Examples of mar include the typical damage found on paint coats and dashboard surfaces damaged by small pointed objects such as rough stones, sticks, keys etc. A scratch is a mark that forms visible grooves and/or surface damage, often referred to as "whitening" of the scratched surface. A scratch is the typical damage mode for surfaces that withstand heavier moving loads. "Whitening" of the scratched surface is a key damage mechanism that has prompted much concern in industries and applications where surface aestheticism or residual strength of the scratched/marred article may be important.

By using a scratch testing device, scratches and/or mars may be made on the surface of a material sample. Analysis of the scratch and/or mar during and after the scratch test may provide useful data and insight into the material properties or surface characteristics of the samples tested. Further, a better understanding of the micromechanical properties of materials, derived from surface testing and analysis, and a better understanding of the mechanical process of surface damage may enable quantitative evaluation in the scratch and/or mar behaviors of various materials under a variety of conditions. For example, scratch tests may indicate the critical load at which whitening occurs at the surface of a given material, or scratch tests may aid in predicting the ability of a given material to withstand scratch and mar surface damage.

Currently, there are limited means and methods recognized for surface testing and analysis. Further, most conventional surface testing devices and methods have some drawbacks. For instance, conventional testing means may yield inconsistent and irreproducible data and results. For example, the stylus of some conventional testing devices may "skip" or "jump" during testing, thereby contributing to inconsistent testing results. Inconsistent and irreproducible data and results may not allow a true comparison between different samples and tests. In addition, the range of loads that can be applied during scratch testing and the range of scratch speeds may be limited in most conventional and commercial devices. Further, conventional devices may not allow for variable load or variable scratch speed testing in a single test. Still further, some conventional scratch testing devices may be unable to measure and capture quantitative data (e.g., load, scratch speed, scratch depth, etc.) during the actual surface test. Many conventional devices merely provide a scratched and/or marred sample for separate study, which is generally qualitative. Without gathering quantitative data during testing, it may not be possible to verify that the intended load conditions and scratch speed actually occurred during testing.

Consequently, there is a need for improved apparatus and methods for surface testing and analysis. In addition, there is a need for surface testing devices and methods which produce reliable and consistent results. Further, needs include improved surface testing apparatus and methods that provide the ability to carry out multi-pass, load-controlled scratch tests with variable scratch speed. Still further, needs include improved surface testing apparatus and methods that measure and capture critical quantitative data (e.g., loads, scratch speed, scratch depth, etc.) during surface testing.

BRIEF SUMMARY OF SOME OF THE PREFERRED EMBODIMENTS

These and other needs in the art are addressed in one embodiment by a scratch testing device for scratch and/or mar testing the surface of a material specimen. In an embodiment, the scratch testing device comprises a scratching member. In addition, the scratch testing device comprises a carriage operable to move the scratching member. Further, the scratch testing device comprises a load mechanism, wherein the load mechanism applies a load to the scratching member.

These and other needs in the art are addressed in another embodiment by a method of scratch testing a material specimen. In an embodiment, the method comprises securing the material specimen to a testing surface. In addition, the method comprises applying a load to a scratching member, wherein said load is applied by a load mechanism. Further, the method comprises positioning said scratching member at a start point. Still further, the method comprises moving said scratching member across the surface of the material specimen from said start point to an end point. Still further, the method comprises analyzing the surface of the material specimen.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

Figure 1:
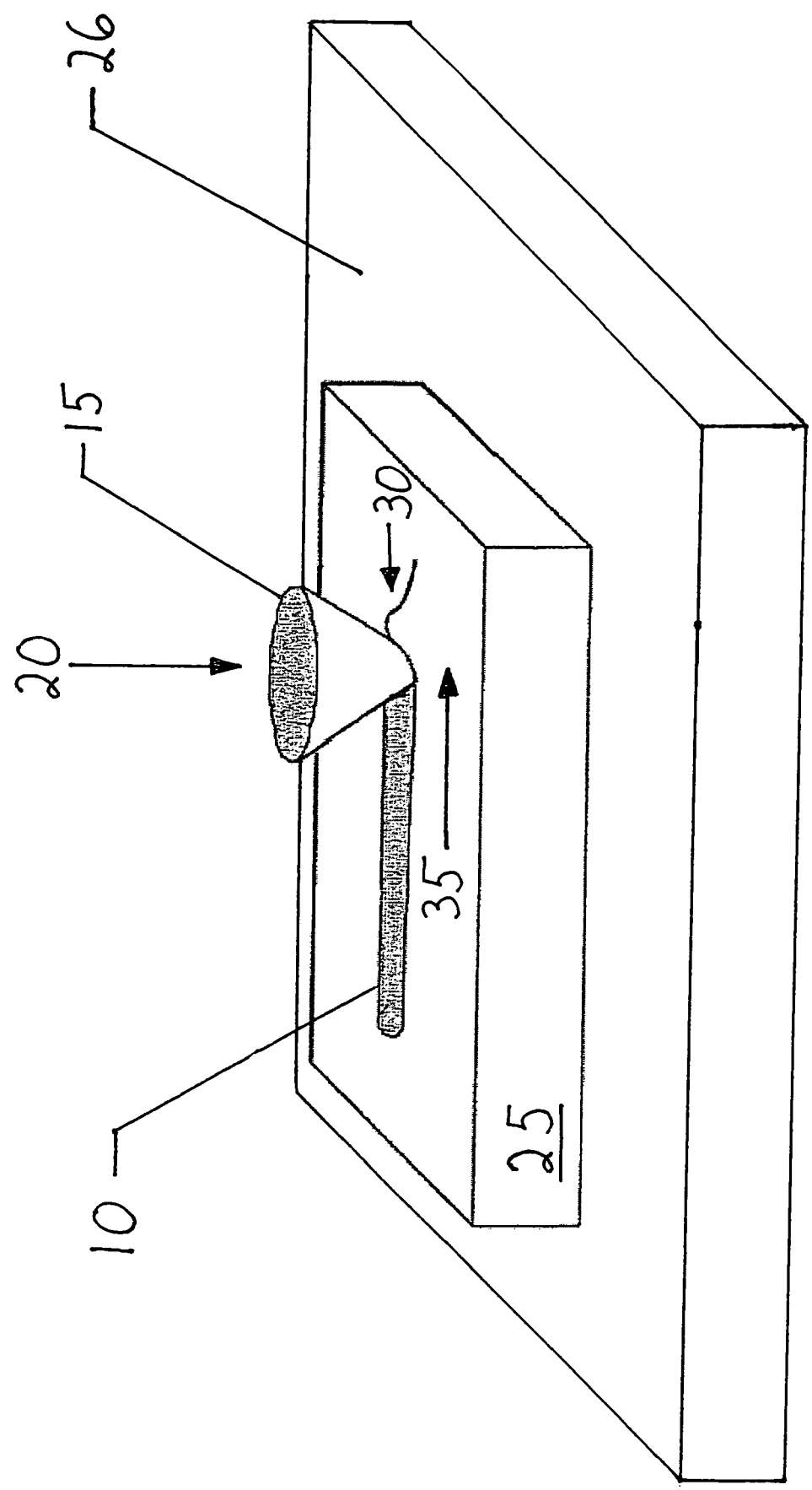
FIG. 1 illustrates a scratch process.

FIG. 1 illustrates a scratch process. A load (20) is applied to a stylus (15) as the stylus (15) moves across the surface of a specimen (25) with a velocity (35). The load (20) is imposed on the stylus (15), tending to push stylus (15) against specimen (25). As a result, a scratch (10) is created in the surface of specimen (25). The scratch (10) results from the mechanical deformation, removal and/or displacement of material from the surface of specimen (25). In general, when the load (20) applied to the stylus (15) is substantially perpendicular to the surface of the specimen (25), the load (20) may be referred to as a "normal load."

A friction force (30) at the interface of the stylus (15) and the specimen (25), acts against the movement of the stylus (15). In general, "friction force" refers to the tangential force present at the interface between the stylus (15) and the specimen (25) when the stylus (15) moves or tends to move relative to the specimen (25), under the action of an external load. Depending on the penetration of the stylus (15) into the test surface of specimen (25), the friction force (30) may be caused by sliding, plastic deformation, cracking, chipping, and/or ploughing (i.e., gross removal/displacement of materials).

In an embodiment as illustrated in FIG. 1, the specimen (25) is supported by a work surface (26) during the scratch process. In an embodiment, the specimen (25) may be secured to the work surface (26) while the stylus (15) moves across the surface of the specimen (25). Specimen (25) may be secured to work surface (26) by any suitable means, including without limitation clamps, screws, etc. In an alternative embodiment (not illustrated), the specimen (25) is not secured to a work surface.

Figure 2:
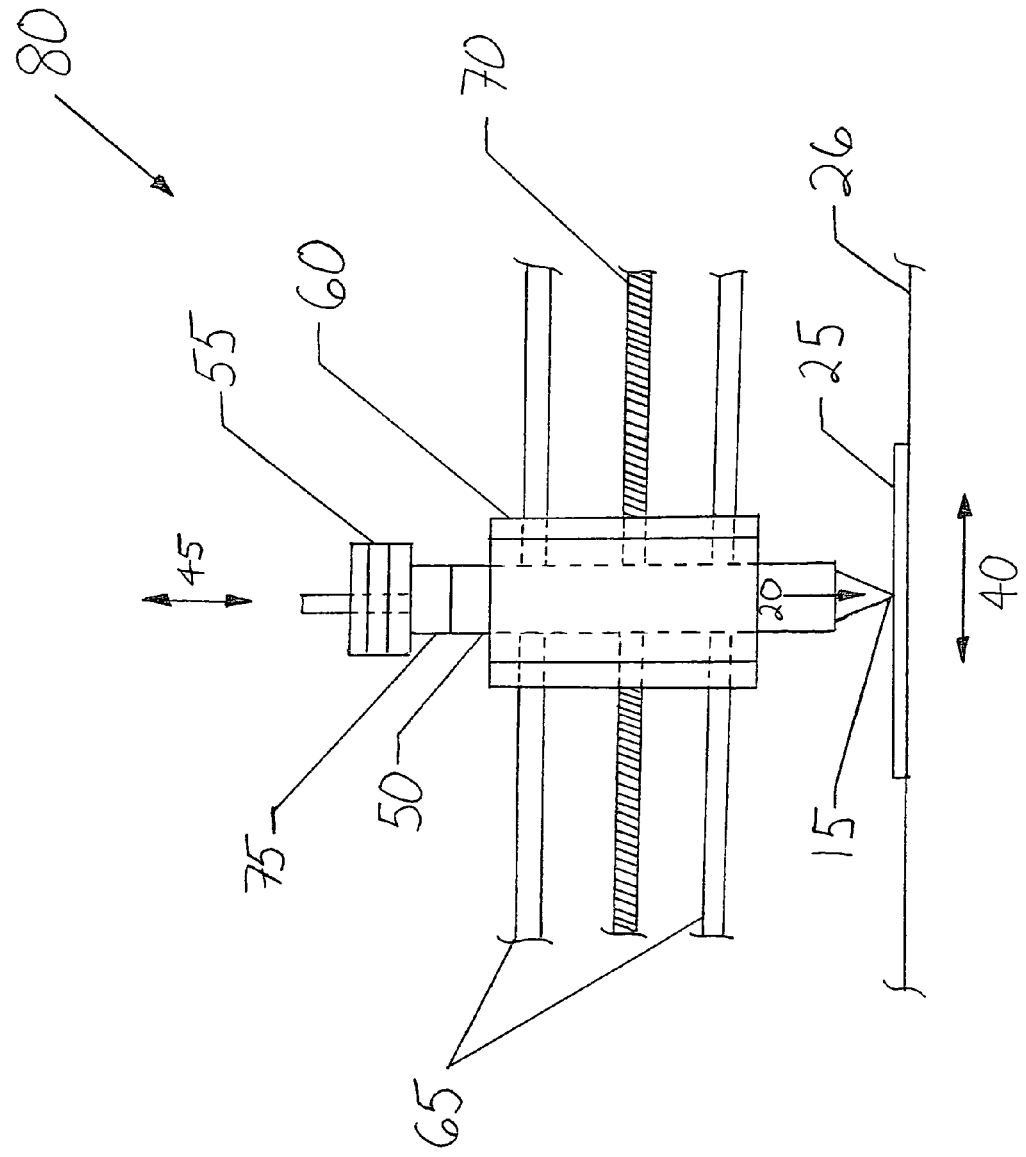
FIG. 2 illustrates a front schematic view of an embodiment of a scratch testing device with a dead-weight load.

FIG. 2 illustrates a scratch testing device (80) comprising a scratching member (50), a carriage (60), and a dead-weight (55). Scratch testing device (80) further comprises guide rods (65), a lead screw (70), and a load sensor (75). Scratching member (50) includes a stylus (15) that contacts the surface of the specimen (25) during surface testing. The stylus (15) is removably fixed to the end of the scratching member (50) nearest the specimen (25).

Figure 3:
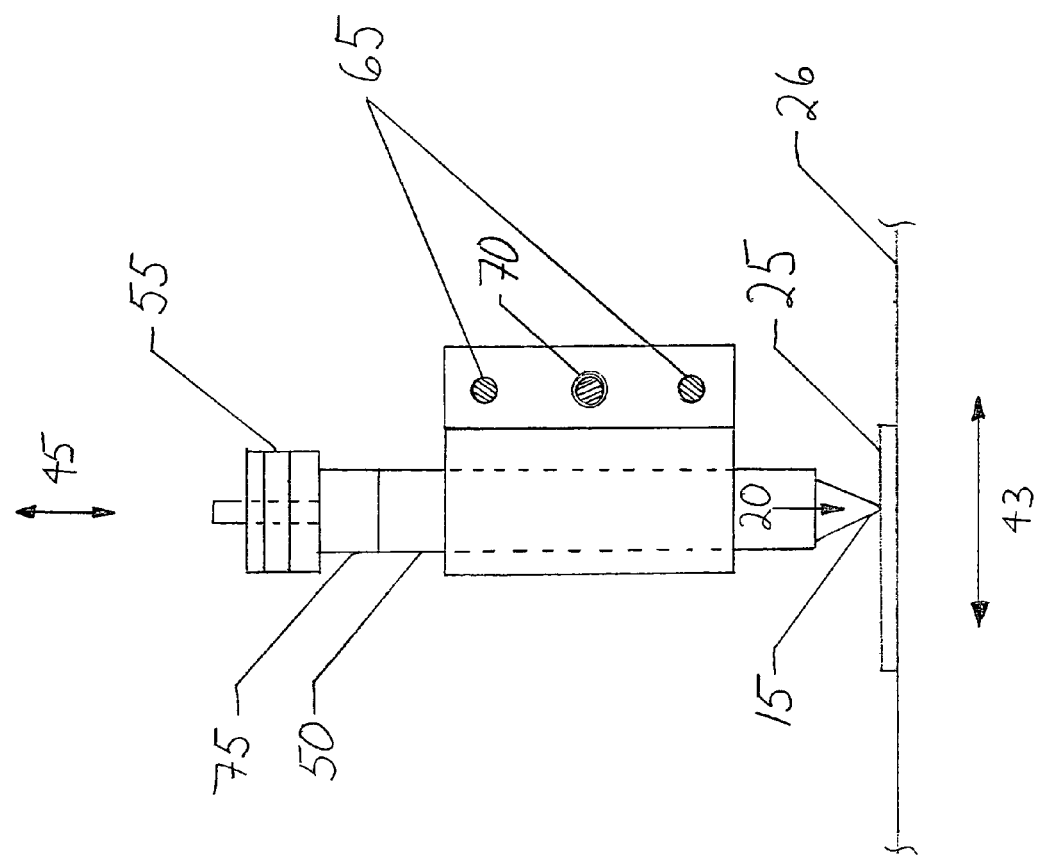
FIG. 3 illustrates an end schematic view of the scratch testing device shown in FIG. 2.

Referring to FIGS. 2 and 3, guide rods (65) and lead screw (70) control the linear motion of the carriage (60) in the x-direction (40). A drive motor (not shown) is coupled to the lead screw (70), such that the drive motor rotates the lead screw (70) in either direction with variable rotational speed. The carriage (60) is coupled to the lead screw (70) with mating threads such that the carriage (60) is forced to move linearly in the x-direction (40) when the lead screw (70) rotates. Further, guide rods (65) guide the linear motion of the carriage (60) in the x-direction (40). The guide rods (65) and the lead screw (70) prevent the carriage (60) from moving in the z-direction (45) and y-direction (43). It is to be understood that the y-direction is orthogonal to both the x-direction (40) and the z-direction (45). By controlling the drive motor (not shown), the position and motion of the carriage (60), the scratching member (50) and the stylus (15) are thereby controlled. Use of the lead screw (70) to control the motion of the carriage (60) may enable very fine and precise control over the position and motion of the carriage (60).

Still referring to FIGS. 2 and 3, the scratching member (50) is slidingly disposed within carriage (60). The scratching member (50) does not move relative to the carriage (60) in the x-direction (40). Thus, as the carriage (60) moves linearly, the scratching member (50) moves linearly with the same speed, acceleration and direction as the carriage (60). However, the scratching member (50) may move relative to the carriage (60) in the z-direction (45) in response to forces acting on the scratching member (50) in the z-direction (45), such as load (20). In the embodiments shown in FIGS. 2 and 3, the scratching member (50) does not move relative to the carriage (60) in the y-direction (43).

The dead-weight (55) is loaded onto scratching member (50) to achieve the desired load (20) acting on the scratching member (50) and stylus (15). The load (20) tends to push the tip of the stylus (15) against the surface of the specimen (25). Depending on the test, the amount of dead-weight (55) placed on scratching member (50) may be varied. A load sensor (75) measures the actual load (20) acting on the scratching member (50) and stylus (15). Load sensor (75) may be any sensor suitable for measuring a load.

Once the desired load (20) is achieved, an operator (not shown) may start the drive motor (not shown) to move the carriage (60) and stylus (15) in the x-direction (40). The location, direction, speed, and acceleration of the stylus (15) may be varied by controlling the drive motor (not shown). Depending on the test to be performed, the stylus (15) may be moved with a constant speed or with a variable speed by adjusting the drive motor (not shown).

Referring to FIG. 2, as the scratching member (50) moves in the x-direction (40), the stylus (15) moves across the specimen (25) in the x-direction (40), thereby creating a scratch and/or mar in the surface of the specimen (25). At the completion of the scratch test, the movement of carriage (60) and stylus (15) may be stopped by controlling the drive motor (not shown). The dead-weight (55) may be removed from the scratching member (50), and the specimen (25) may be removed from the work surface (26) for further examination.

In another embodiment (not illustrated), a spring-loaded mechanism, rather than a dead-weight, is used to provide a load to the stylus. The load transmitted by the spring-loaded mechanism may be a constant load or a variable load during the test. Not being limited by theory, inclusion of a spring reduces the occurrence of chattering and jumping of the stylus and aids in maintaining the stylus in constant contact with the specimen. In addition, by using a spring to transmit the load to the specimen, small variations in the thickness of the specimen may be accommodated by the scratch testing device.

Figure 4:
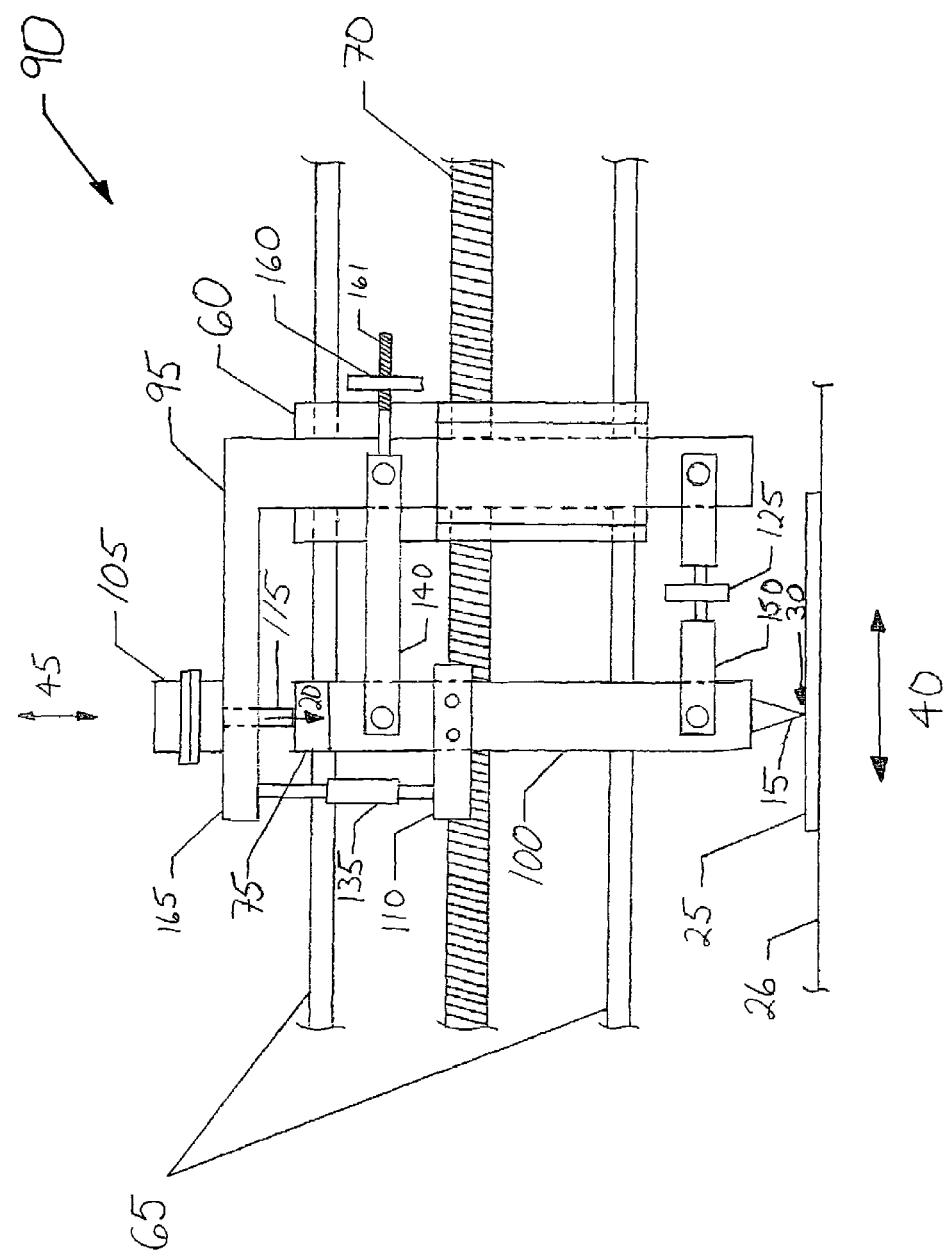
FIG. 4 illustrates a front schematic view of an embodiment of a scratch testing device with variable load and variable scratch speed capability.

FIG. 4 illustrates a scratch testing device (90) comprising a scratching member (100), a load generating device (105), and a carriage (60). Scratch testing device (90) further comprises guide rods (65), a lead screw (70), a leading member (95), an upper linking arm (140), and a lower linking arm (150). The load generating device (105) includes a plunger (115) that extends from the load generating device (105) and transfers forces to the scratching arm (100). The scratching member (100) includes a stylus (15) that contacts the surface of the specimen (25) during the surface testing. The stylus (15) is removably fixed to the end of scratching member (100) nearest the specimen (25). Still further, the scratch testing device (90) comprises a plurality of sensors including a load sensor (75), a scratch depth sensor (135), a linear load sensor (125), and a linear position sensor (not shown).

The guide rods (65) and lead screw (70) control the linear motion of the carriage (60) in the x-direction (40). A drive motor (not shown) is coupled to the lead screw (70), such that the drive motor rotates the lead screw (70) in either direction with variable rotational speed. The carriage (60) is coupled to the lead screw (70) with mating threads such that the carriage (60) is forced to move linearly in the x-direction (40) when the lead screw (70) rotates. Further, guide rods (65) guide the linear motion of the carriage (60) in the x-direction (40). The guide rods (65) and the lead screw (70) prevent the carriage (60) from moving in the z-direction (45) and y-direction (43). It is to be understood that the y-direction is orthogonal to both the x-direction (40) and the z-direction (45). By controlling the drive motor (not shown), the position and motion of the carriage (60), the scratching member (50) and the stylus (15) are thereby controlled. Use of the lead screw (70) to control the motion of the carriage (60) may enable very fine and precise control over the position and motion of the stylus (15).

In certain embodiments (not illustrated), the drive motor and lead screw are capable of varying the linear speed of the stylus (15) anywhere from about 0 to about 600 mm/s, or alternatively from about 1 to about 400 mm/s; and varying the acceleration of stylus (15) from about 0 to about 25,000 mm/s$^2$. Further, as one skilled in the art understands, the drive motor used to move and control stylus (15) may be any suitable device capable of moving a stylus under a load, including without limitation electric motors, hydraulic actuators, internal combustion engines, etc. Still further, the drive motor may be coupled to lead screw (70) directly or indirectly through gears, belts, pulley system, etc.

Although one lead screw (70) and two guide rods (65) are shown in FIGS. 2, 3, and 4, in other embodiments, more than one lead screw (70) and/or one or more guide rods (65) may be provided to control the position and motion of stylus (15). Further, although the guide rods (65), the lead screw (70), and the drive motor (not shown) are used to control the position and motion of stylus (15) in FIGS. 2, 3, and 4, any suitable means of controlling the position and motion of stylus (15) may be employed including without limitation geared systems, track systems, etc.

Referring to FIG. 4, the leading member (95) is fixed to the carriage (60) such that the leading member (95) does not move transitionally or rotationally relative to the carriage (60). Thus, as the carriage (60) moves linearly in response to the rotation of lead screw (70), the leading member (95) moves linearly with the same speed, direction and acceleration as the carriage (60).

Scratching member (100) is pivotally connected to the leading member (95) by the upper linking arm (140) and lower linking arm (150) such that scratching member (100) may move in the z-direction (45) relative to the leading arm (95) and carriage (60). Scratching member (100) may move in the z-direction (45) in response to forces acting on the scratching member (100) in the z-direction (45), such as load (20) and counterweight (160).

The upper linking arm (140) and lower linking arm (150) transfer the linear motion of leading member (95) to the scratching member (100). Thus, as the carriage (60) moves linearly in the x-direction (40), the stylus (15) moves linearly in the x-direction (40) at substantially the same speed, acceleration and direction as the carriage (60).

Still referring to FIG. 4, a counterweight (160) is provided on an extension (161) of the upper linking arm (140). The extension (161) is fixed relative to the upper linking arm (140). Further, the extension (161) is threaded to mate with threads in the counterweight (160) such that the counterweight (160) may be moved along the extension (161) by rotating the counterweight (160) in either direction. In a different embodiment (not illustrated), a second counterweight is provided adjacent counterweight (160) such that when both counterweights are in contact with each other they become effectively thread locked, thereby ensuring that the counterweights do not move relative to the extension (161) during a surface test.

Not being limited by theory, the counterweight (160) is positioned along extension (161) to zero out the weight of scratching member (100) and to maintain the scratching member (100) and load sensor (75) in near contact with plunger (115). As one skilled in the art understands, any suitable means may be employed to balance the weight of the scratching arm (100) and to maintain the scratching arm (100) in near contact with the load generating device (105).

The load generating device (105) transmits a load (20) to the scratching member (100) through the plunger (115). The load (20) tends to push the stylus (15) against the surface of the specimen (25). Further, the load generating device (105) is capable of providing a constant or variable load (20) (e.g., increasing load during testing, decreasing load during testing, etc.). The load generating device (105) may be any suitable device capable of providing a load to the scratching member (100) and the stylus (15), including without limitation a pneumatic diaphragm, a hydraulic actuator, a spring-loaded mechanism, an electrical actuator, etc. In a different embodiment (not illustrated), one device may serve as both the drive motor (not shown) and the load generating device. Although the embodiments shown in FIGS. 1-4 show load (20) as substantially perpendicular to the surface of specimen (25), in other embodiments (not illustrated), the load (20) may be applied at an angle other than perpendicular to the surface of the specimen (25).

Still referring to FIG. 4, the load generating device (105) is separate from, and not supported by, the scratching member (100). Not being limited by theory, this configuration reduces vibrations that might otherwise be transmitted into the test specimen (25).

The load sensor (75) measures the actual load (20) acting on stylus (15) during testing. The load sensor (75) may be any suitable device capable of measuring a linear force.

A linear load sensor (125) is provided along the lower linking arm (150) to measure the friction force (30) acting on the stylus (15) during testing. As the leading member (95) moves linearly, a force (not shown) is transferred through upper linking arm (140) and lower linking arm (150) to scratching member (100), thereby inducing scratching member (100) to move in the x-direction (40). However, as the stylus (15) is pulled along the surface of specimen (25), a friction force (30) acts against the linear movement of the stylus (15). The linear load sensor (125) measures the friction force (30) acting against stylus (15). The linear load sensor (125) may be any suitable device capable of measuring a linear force.

A scratch depth sensor (135) is provided adjacent the scratching member (100), between the end (165) of the leading member (95) and the scratching member arm (110). The scratching member arm (110) is fixed to the scratching member (100) such that scratching member arm (110) does not move translationally or rotationally relative to the scratching member (100). The end (165) of the leading member (95) moves linearly in the x-direction (40), but does not move in the z-direction (45) or y-direction (not shown) relative to the carriage (60). Thus, the scratch depth sensor (135) measures the displacement, in the z-direction (45), of the scratching member (100) and stylus (15) during testing. By measuring the actual displacement of the stylus (15) in the z-direction (45), scratch depth sensor (135) measures the depth of the scratch or mar created in the surface of specimen (25) during testing.

The location, direction, speed, and acceleration of the carriage (60), and hence the stylus (15), are controlled by adjusting the drive motor (not shown). Depending on the test to be performed, the stylus (15) may be moved with constant speed or variable speed. A linear position sensor (not shown) measures the actual location, direction, speed, and acceleration of stylus (15) in the x-direction (40) during the test.

Still referring to FIG. 4, as the scratching member (100) moves linearly in the x-direction (40), the stylus (15) moves across the specimen (25) in the x-direction (40), thereby creating a scratch and/or mar in the surface of specimen (25). At the completion of the scratch test, the movement of the stylus (15) may be stopped by controlling the drive motor (not shown). Further, the load (20) may be removed from the scratching member (100) by controlling the load generating device (105).

Once the test is completed, the specimen (25) may be removed from the work surface (26) for further examination. The surface of the specimen (25) may be visually examined or examined with other evaluation instruments including without limitation optical microscopes, flatbed scanners, image capturing tools, etc. Further, the scratch and/or mar width, as well as the scratch and/or mar depth, may also be quantified visually or with evaluation instruments. "Scratch/Mar depth" refers to the vertical distance to be measured from the trough of the scratch/mar groove to (a) its peak, or (b) to the undisturbed specimen surface, whereas "scratch/mar width" refers to the horizontal distance between the two peaks on both sides of the scratch/mar groove.

Figure 5:
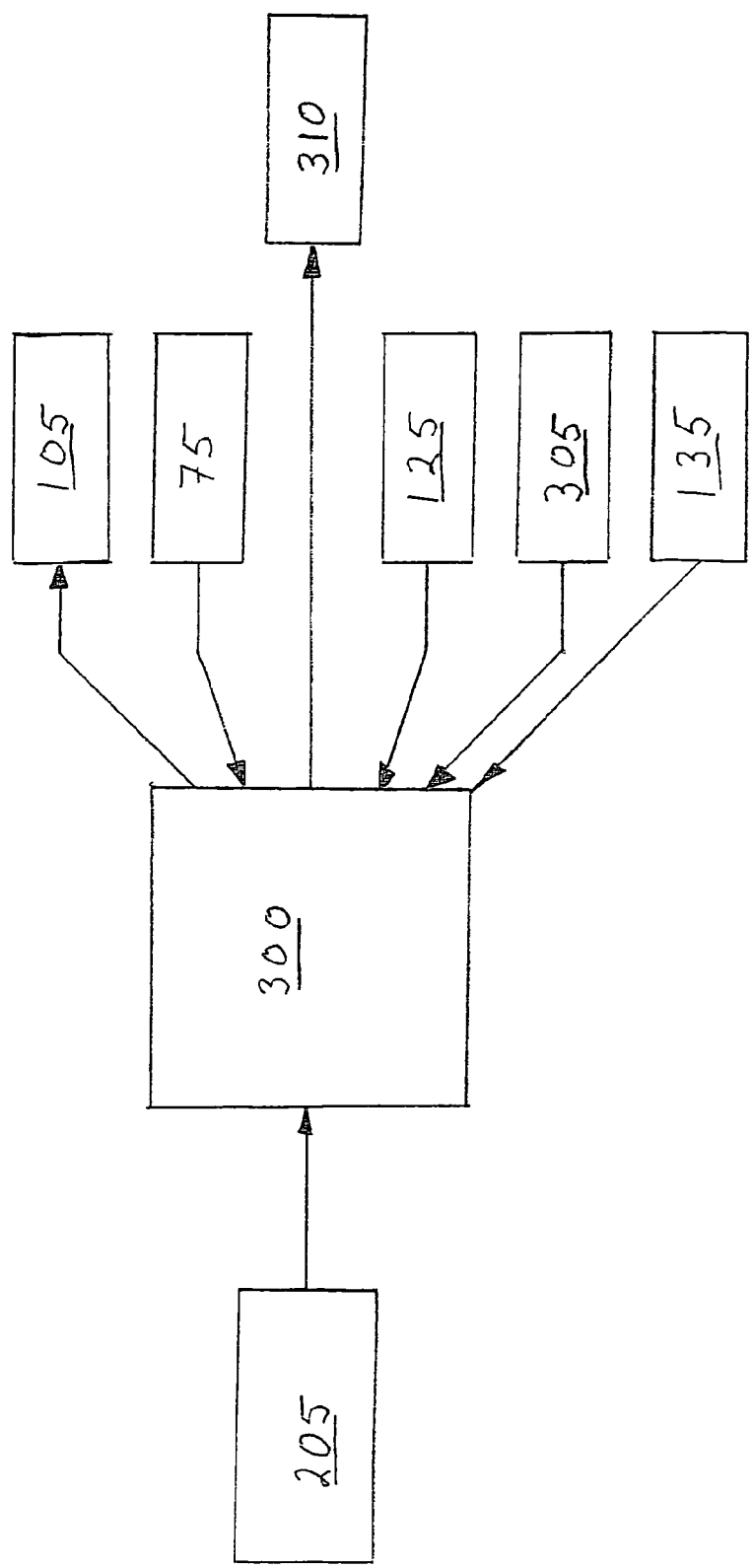
FIG. 5 illustrates a control system used to control a scratch testing device.

A control system (200), illustrated in FIG. 5, may be used to control and automate the scratch testing device (90) illustrated in FIG. 4.

FIG. 5 illustrates a control system (200) comprising a set of testing parameters (205), a control center (300), a load generating device (105), a drive motor (310), and a plurality of sensors, including a load sensor (75), a scratch depth sensor (135), a linear load sensor (125), and a linear position sensor (305). In other embodiments (not illustrated) additional sensors may be included to measure various test conditions including without limitation temperature, drive motor power, etc.

The control system (200) may be used to control the scratch testing device (90) illustrated in FIG. 4. The control system (200) may also be used to control other embodiments of the scratch testing device.

A power supply (not shown) provides power to each of the components of the control system (200). The power supply may be any suitable device for providing power to the components of the control system (200), including without limitation an electrical power supply, a generator, etc. Further, in certain embodiments, the power supply is built as a separate, enclosed, unit in order to reduce the possibility of electrical interference or noise contamination of the testing data.

Before testing, an operator (not shown) inputs a set of testing parameters (205) into the control center (300). The set of testing parameters (205) may include, without limitation, the number of scratch passes, the start and end positions of the stylus, the speed and direction of the stylus during testing (constant or variable), the desired loads to be placed on the stylus during testing (constant or variable), the sampling rate for measurements of scratch depth, the sampling rate for measurements of the linear location, direction, speed, and acceleration of stylus, the sampling rate for measurements of the friction force acting against the motion of the stylus, and the sampling rate for measurements of the load acting on the stylus, etc. In certain embodiments of the control system (200), the sampling rate for data acquisition may range from one to over 5,000 data points per second, per sensor.

The control center (300) is a computer that runs software designed to control the various functions of the scratch testing device (90), to capture a set of actual test data during the scratch test, and to provide data processing and analysis capabilities. The software provides the user interface to the control system (200). For example, the user may use the software to input a set of testing parameters (205) into the control center (300), to initiate the scratch test, to stop the scratch test, and/or to process and analyze the set of actual test data captured during the scratch test. Further, the control center (300) incorporates hardware (not shown) which interfaces with the plurality of sensors of control system (200). In an embodiment (not illustrated), the control center (300) offers network connectivity and the ability to save, backup, and share scratch test data.

The control center (300) receives and records a set of actual test data from the plurality of sensors. The set of actual test data includes without limitation the scratch depth data from the scratch depth sensor (135), the frictional force data from the linear load sensor (125), the load data from load sensor (75), and the stylus (15) location, speed, acceleration, and direction from the linear position sensor (305). Further, the control center (300) controls the load generating device (105) to adjust the load (20) acting on the stylus (15), and controls the drive motor (310) to adjust the location, direction, speed, and acceleration of the stylus (15).

The linear position sensor (305) measures and provides the actual location, direction, speed, and acceleration of the stylus (15) to the control center (300). In certain embodiments, the linear position sensor (305) measures stylus (15) actual position within 5 µm or less, and measures the stylus (15) actual speed within 0.0005 m/s or less. The scratch depth sensor (135) measures and provides the actual scratch/mar depth to the control center (300). In certain embodiments, the scratch depth sensor (135) measures actual scratch/mar depth within 1 µm or less. The load sensor (75) measures and provides the actual load (20) acting on the stylus (15) to control center (300). The linear load sensor (125) measures and provides the actual friction force (30) acting on the stylus (15) to the control center (300). In certain embodiments, the load sensor (75) and the linear load sensor (305) may measure the actual load (20) and the actual friction force (30), respectively, within 0.1 N for a load range from about 0 to over 1,000 N.

In addition, the control system (200) provides a feedback control loop for the scratch testing device (90). By constantly or periodically comparing the set of testing parameters to the set of actual test data (i.e., test conditions measured by the plurality of sensors), the control center (300) can adjust the drive motor (310) and the load generating device (105) to achieve the desired set of testing parameters. For example, by comparing the measured actual location, direction, speed, and acceleration of the stylus (15) with the desired location, direction, speed, and acceleration of the stylus (15) (e.g., which may be input as part of the set of testing parameters), the control center (300) may adjust drive motor (310) to consistently achieve the desired location, direction, speed, and acceleration of the stylus (15). Further, by comparing the measured actual load (20) with the desired load (e.g., which may be input as part of the set of testing parameters), control center (300) can adjust the load generating device (105) to consistently achieve the desired load acting on stylus (15).

By acting as a feedback control loop, control system (200) allows for greater variation in the permissible geometries of the specimen to be tested (i.e., specialized specimen are not required). In some embodiments, the scratch testing device (90) can accommodate and test specimens with thicknesses ranging from about 0 to about 200 mm, or alternatively from about 0.2 mm to about 10 mm. Further, the thickness of the specimen may be constant or variable about the specimen length or width. Still further, the shapes of the specimen may include without limitation round discs, flat plaques or bars, strips, blocks, cubes, tensile bars, impact bars, etc. In addition, the scratch test device (90) can accommodate specimen of varying surface texture and/or roughness. In certain embodiments, the scratch testing device (90) can accommodate specimen (25) whose surface height ranges from about 0.25 mm below to 0.25 mm above the average specimen (25) surface height. Since control center (300) receives a set of measured actual test data from a plurality of sensors, and since control center (300) controls the drive motor (310) and the load generating device (105), adjustments may be made automatically during testing to compensate for such variations in the geometry of the specimen (25).

In addition, by utilizing the control system (200) to monitor and control a scratch testing device (90), the scratch or mar test may be completely automated. Once the operator inputs the desired set of testing parameters (205) and initiates the test, control center (300) signals the drive motor (310) to place the stylus (15) at the desired initial position and signals the load generating device (105) to apply the desired initial load (20). Then, the control center (300) controls the drive motor (310) and load generating device (105) to perform the scratch test in accordance with the set of testing parameters (205). During the scratch test, the control center (300) receives and stores the set of actual test data from the plurality of sensors. When the scratch test is complete, the control center (300) signals the drive motor (310) to stop and signals the load generator (105) to reduce the load (20), thereby allowing stylus (15) to retract from the specimen (25). At this point, any number of additional scratch tests may be automatically performed. By including the capability of automatic test cycles, the amount of training, skill and expertise required to successfully operate a scratch testing device may be reduced. Further, automation of the scratch testing device may enable faster scratch testing, reduce the number of errors in scratch testing, and enhance the accuracy and consistency of the testing data.

After testing, the data recorded and stored in the control center (300) may be processed and analyzed by the software loaded in the control center (300). Without limitation, the software may display actual test data, graphically display various test results (e.g., scratch depth/width vs. linear displacement; scratch depth/width vs. load, etc.), calculate certain test conditions (e.g., the scratching coefficient of friction), etc.

Further, in a different embodiment (not illustrated), an amplifier unit is coupled to each sensor of the control system (200). The amplifier unit may supply power to each sensor. Further, the amplifier unit may receive measured data signals from the sensors, and amplify those signals to a level appropriate for transmission to control center (300). Still further, the amplifier unit may filter noise from the sensor measured data signals. In addition, the amplifier unit may be built as a separate, enclosed unit in order to reduce the effects of electrical interference.

In general, the stylus (15) shown in FIGS. 1-4, may be any device capable of scratching and/or marring the surface of a specimen (25). Although the stylus (15) is shown as having a point in FIGS. 1-4, in different embodiments (not illustrated), the stylus (15) may be of any suitable geometry (e.g., round, square, etc.). Further, the stylus (15) may be composed of any suitable material capable of scratching and/or marring the surface of a specimen (25), including without limitation metals and metal alloys (e.g., steel, iron, aluminum, etc.) and non-metals (composites, plastics, wood, etc.). Still further, the stylus (15) may be hardened, coated, and/or impregnated. For example, stylus (15) may be heat treated or impregnated with diamond cuttings to enhance its hardness.

Further, as shown in FIGS. 2-4, the stylus (15) is removably fixed to the scratching member. Thus, stylus (15) may be removed from the scratching member and replaced with a different stylus (15). Since styli may be of numerous geometries, material composition, etc., a variety of different testing conditions may be possible by replacing one stylus with a different stylus. In certain embodiments (not illustrated), the stylus (15) may be permanently fixed to scratching member (50). Further, in another embodiment (not illustrated), scratching member (50) includes more than one stylus (15).

In some embodiments (not illustrated), the scratch testing device may be disposed within an environmental chamber in which various environmental conditions, including without limitation temperature and humidity, may be controlled so that scratch tests may be performed under specified environmental conditions. In certain embodiments (not illustrated), the environmental chamber may control the temperature anywhere between −100 to 150° C.

In certain embodiments (not illustrated), the work surface and the scratch testing device are supported by a frame which provides a strong, vibration-free mounting location. The frame may be made from any suitable material(s). For instance, the frame may be made from interlocking (mortise-and-tenon) steel plates, which are then welded into a solid assembly, thereby providing an exceptionally strong base for the scratch testing device and the working surface (26). In general, the increased stiffness of the frame enhances the precision of the machine. In addition, the base of the frame may include adjustable feet so that the work surface (26) and scratch testing device may be leveled on an uneven floor. Further, the scratch testing device may be mounted to the frame with vibration isolating bushings to prevent the transfer of undesirable vibrations.

Although the examples to follow describe the scratch testing device in regard to polymer testing, other embodiments of the scratch testing device may be used to test other materials, including without limitation metals, non-metals, composites, films, coatings (e.g., painted, polished, or plated surfaces), etc. In particular, the scratch testing device is especially useful for evaluating and studying materials where cosmetic or surface damage is important, such as automotive parts (bumpers, body panels, dashboards, etc.), furniture (table-tops, etc.), durable goods (electronics, cellular phones, etc.), packaging (product bottles, containers, or film laminates), etc. In addition, the scratch testing device is also useful for other fields including optics, eyeglasses, semiconductors, etc.

In the manner described, the scratch testing device may be used to perform scratch, mar, and wear-resistance testing on various material samples. In certain embodiments, the scratch testing device has the capability to execute multi-pass tests, constant or variable load tests, constant or variable stylus speed tests, or any combination thereof using a range of styli. In addition, since certain embodiments of the scratch testing device are computer controlled and automated, the training required before an operator can begin testing with the device are reduced. Further, due to the modular design of certain embodiments, reconfiguration of the scratch testing device for different samples or different types of tests is relatively simple. Different sensors, drive motors, and/or load generating devices may be swapped in and out, thereby enabling the scratch testing device to be re-configured for different test conditions.

The apparatus and methods for scratch testing materials described overcomes problems with conventional scratch testing devices. For instance, certain embodiments of the scratch testing device are instrumented. In other words, these embodiments of the scratch testing device have a plurality of sensors that take measurements and gather quantitative data during testing. Thus, the scratch testing device may be used for quantitative as well as qualitative experiments. Further, some embodiments of the scratch testing device are load-controlled. In these embodiments, the load imposed on the stylus (15) is precisely controlled (constant or variable during testing). Consequently, the scratch testing device is capable of performing a linearly rising load scratch test (i.e., the load applied to the stylus (15) increases as the stylus (15) moves during testing). Not being limited by theory, by having control over the load, the immediate point at which the scratch or mar first occurs may be identified and compared to recorded test data to provide information such as the position at which the scratch occurred and the load applied at such position. Still further, certain embodiments of the scratch testing device are position specific. When operating such embodiments, a set of testing parameters (e.g., start and stop positions, stylus speed, stylus direction, etc.) are pre-determined and maintained in a control system. Comparison of the set of testing parameters to a set of actual test data, and subsequent control of the scratch testing device in response to differences between the testing parameters and test data enable the control system to maintain the actual testing conditions within a tight tolerance relative to the testing parameters. This enhances the stability, consistency and repeatability of test conditions regardless of material properties. Without being limited by theory, this permits for a true comparison of scratch test results between different materials.

While preferred embodiments of this invention have been shown and described, modifications thereof can be made by one skilled in the art without departing from the scope or teaching of this invention. The embodiments described herein are exemplary only and are not limiting. Many variations and modifications of the system and apparatus are possible and are within the scope of the invention. For example, the relative dimensions of various parts, the materials from which the various parts are made, and other parameters can be varied, so long as the reverse rotation prevention device retains the advantages discussed herein. Accordingly, the scope of protection is not limited to the embodiments described herein, but is only limited by the claims that follow, the scope of which shall include all equivalents of the subject matter of the claims.

EXAMPLE 1

To assess the frictional force and determine the scratching coefficient of friction of a polypropylene with talc filler specimen, controlled scratch tests were administered with a scratch testing device having a variable load generating device, a scratch depth sensor, a linear load sensor, and a load sensor. Real time data such as scratch distance, load, and friction force, respectively were captured during the scratch process.

Figure 6:
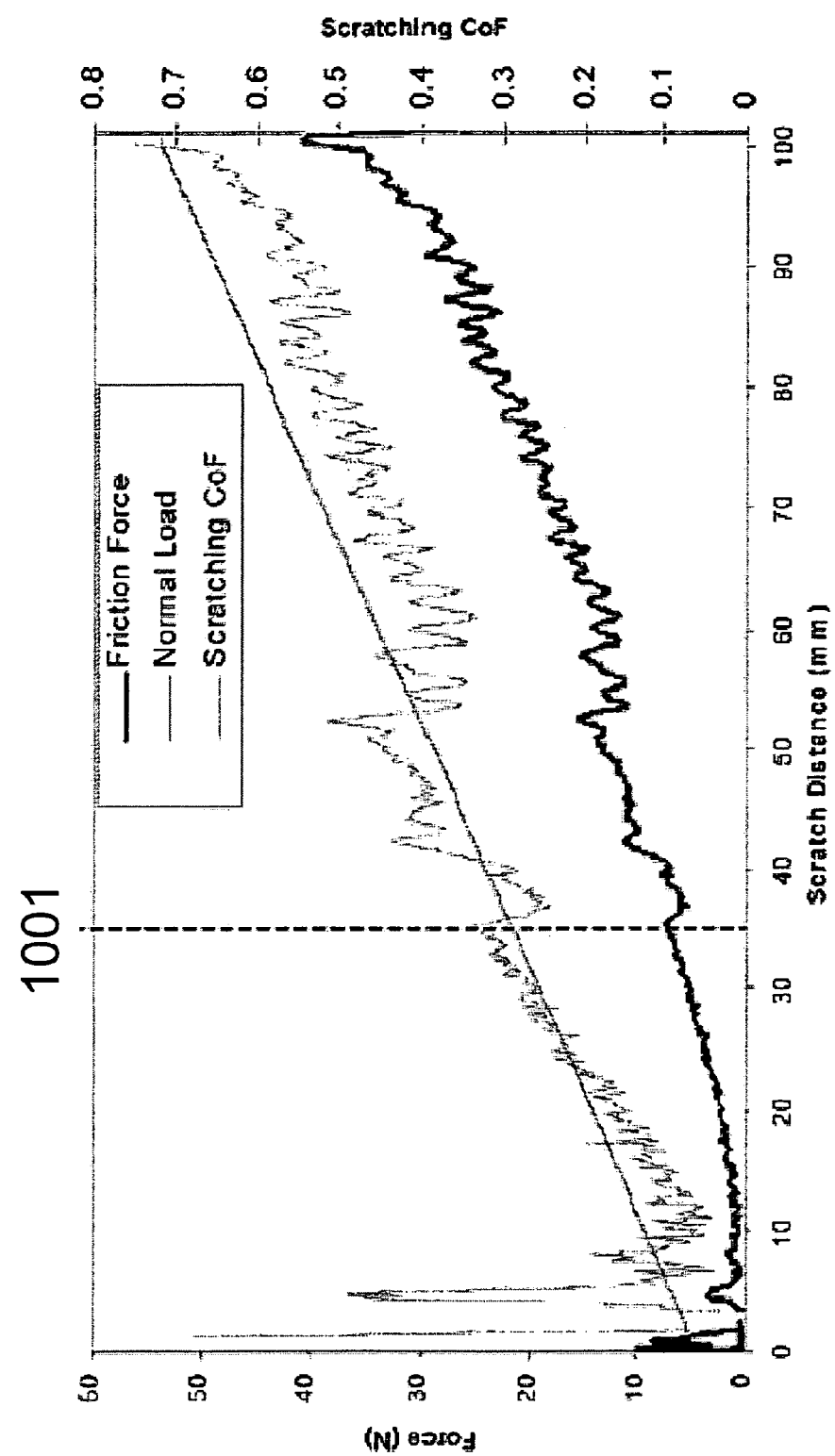
FIG. 6 illustrates a graphical plot of frictional force and the scratching coefficient of friction vs. scratch distance.

The scratching coefficient of friction, which represents the resistance of a material to scratching, was calculated from the ratio of the friction force to the normal load. The frictional force and scratching coefficient of friction were then graphically plotted as a function of scratch distance as shown in FIG. 6. For this particular test, a scratch was applied on a polypropylene specimen under an increasing load from 2.0 to 50.0 N±0.1 N over a distance of 0.1 m±10.0005 m at a constant rate of 0.1 m/s±10.0005 m/s. Dashed line (1001) represents the point at which whitening was observed in the test specimen. The load measured during testing was referred to as "Normal Load" in FIG. 6.

As shown in FIG. 6, during the test, the initial measured load was between 0.5 and 5 N and steadily increased to a maximum measured load of about 50 N. Further, as the measured load increased during testing, the average measured frictional force also increased from between 0 to 10 N initially (due to a transition from static friction to dynamic friction) to a maximum of about 40 N near the completion of the test.

EXAMPLE 2

Figure 7:
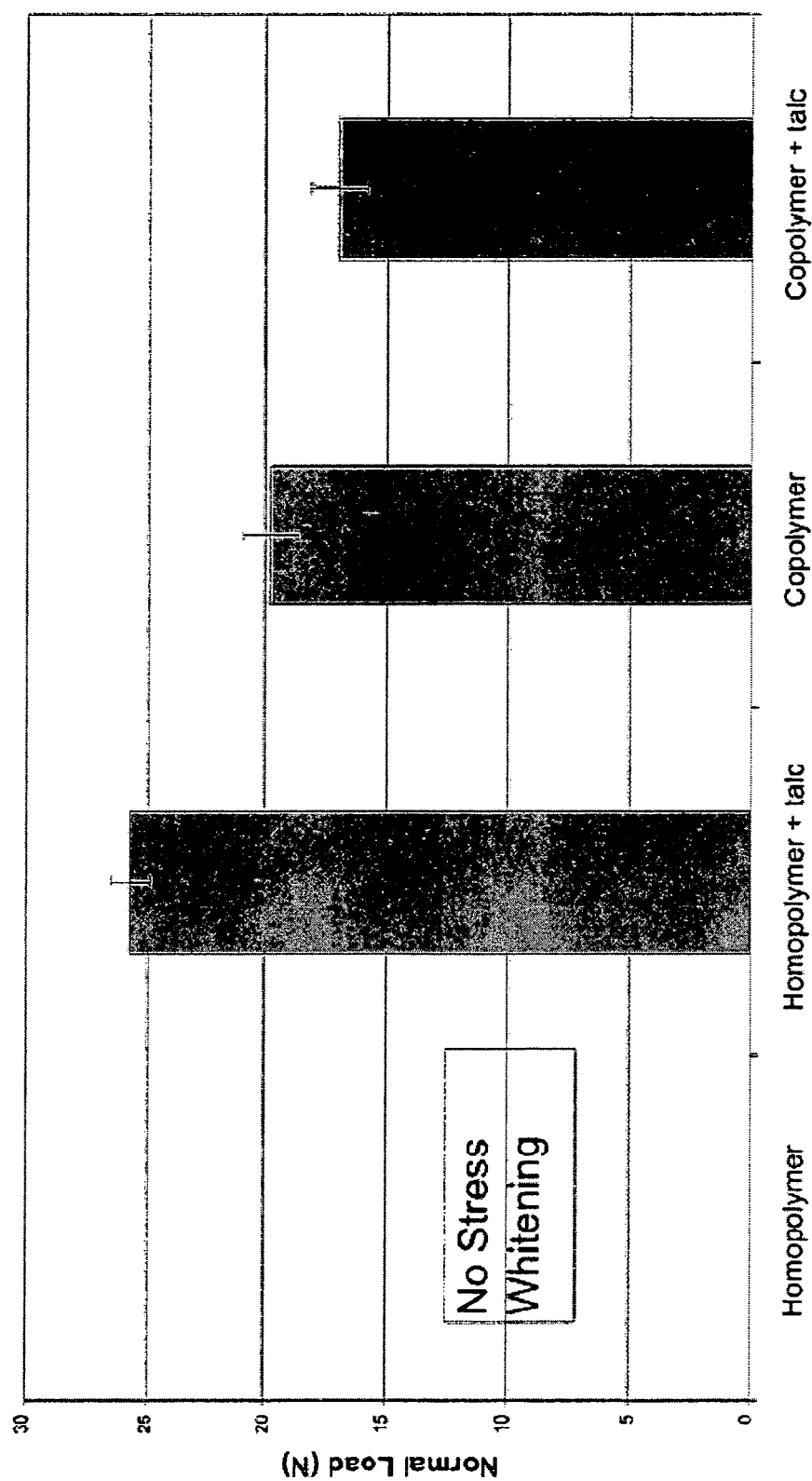
FIG. 7 illustrates a bar graph of the critical load for scratch visibility of various polymer systems.

To assess the load at which whitening occurred (i.e., the critical load) for different polypropylene systems, controlled scratch tests were administered with the scratch testing device of Example 1. For this example, a scratch was applied to different material specimens under an increasing load from 2.0 to 50.0 N±0.1 N over a distance of 0.1 m±0.0005 m at a constant rate of 0.1 µm/s±0.0005 m/s. To determine the critical point for the onset of whitening, image capturing equipment, VIEEW, was utilized with a consistent set of light and grey-scale settings. The VIEEW digital image analyzer is manufactured by Atlas (http://www.atlas-mts.com). FIG. 7 illustrates the critical normal load at which the onset of whitening begins for various polymer systems.

As shown in FIG. 7, for the homopolymer polypropylene specimen (no filler), no whitening was apparent on the sample after the test. For the polypropylene with talc filler specimen, whitening occurred at a critical normal load around 26 N. For the copolymer polypropylene specimen, whitening occurred at a critical normal load just below 20 N. For the copolymer polypropylene with talc filler specimen, whitening occurred between 16 and 17 N.

EXAMPLE 3

To assess the repeatability and reproducibility of the scratch testing device of Example 1, controlled scratch test were administered. A scratch was applied on a polypropylene specimen under an increasing load from 2.0 to 50.0 N±0.1 N over a distance of 0.1 m±0.0005 m at a constant rate of 0.1 μm/s±0.0005 m/s.

Two test runs with the scratch testing device were conducted. Each test run was based on the average of three tested samples. The test runs were conducted by the same operator under the same operating conditions using the same scratch testing device on the same day. Table 1 below shows the results of this test. For Test Run 1, the average load at which whitening occurred was 6.79 N, with a standard deviation of ±0.26 N. For Test Run 2, the average load at which whitening occurred was 6.61 N, with a standard deviation of ±0.38N.

TABLE 1

Repeatability Data - Critical Normal Load for Whitening (Single Operator)

| Test Run | Average | $S_r^A$ |
|---|---|---|
| 1 | 6.79 | ±0.26 |
| 2 | 6.61 | ±0.38 |

In addition, a round-robin test involving three operators was conducted under the same conditions (increasing load from 2.0 to 50.0 N±10.1 N over a distance of 0.1 m±0.0005 m at a constant rate of 0.1 m/s±0.0005 m/s). The test results were based on the average of five tested samples. The round-robin test was conducted by three operators under the same operating conditions using the same scratch testing device on the same day. Table 2 below shows the results of this round-robin test. For Operator I, the average load at which whitening occurred was 6.64N, with a standard deviation of ±0.26N. For Operator II, the average load at which whitening occurred was 6.72N, with a standard deviation of ±0.18N. For Operator III, the average load at which whitening occurred was 6.80N, with a standard deviation of ±0.20N.

TABLE 2

Reproducibility Data - Critical Normal Load for Whitening (Three Operators)

| Operator | Average | $S_r^A$ |
|---|---|---|
| I | 6.64 N | ±0.26 N |
| II | 6.72 N | ±0.18 N |
| III | 6.80 N | ±0.20 N |

EXAMPLE 4

To assess the repeatability and reproducibility of the scratch testing device of Example 1, controlled scratch tests were administered on polypropylene specimens to determine the scratching coefficient of friction. A scratch was applied onto a polypropylene specimen surface under a constant load of 30 N±0.1N over a distance of 0.1 m±0.0005 m/s at a constant rate of 0.1 m/s±0.0005 m/s.

Real time data such as scratch length, load, and friction force, respectively were captured during the scratch process. The scratching coefficient of friction, which represents the resistance of a material to scratching, was calculated from the ratio of the friction force to the load.

Two test runs with the scratch analysis device were conducted. Each test run was based on the average of three tested samples. The test runs were conducted by the same operator under the same operating conditions using the same machine on the same day. Table 3 below shows the results of this test. For Test Run 1, the average scratching coefficient of friction was 0.430, with a standard deviation of ±0.012. For Test Run 2, the average scratching coefficient of friction was 0.433, with a standard deviation of ±0.040.

TABLE 3

Repeatability Data - Scratching Coefficient of Friction (Single Operator)

| Test Run | Average | $S_r^A$ |
|---|---|---|
| 1 | 0.430 | ±0.012 |
| 2 | 0.433 | ±0.014 |

In addition, a round-robin test involving three operators was conducted under the same conditions (constant load of 30.0 N±0.1N over a distance of 0.1 m±0.0005 m/s at a constant rate of 0.1 μm/s±0.0005 m/s ). The test results were based on the average of five tested samples. The round-robin test was conducted by three operators under the same operating conditions using the same scratch testing device on the same day. Table 4 below shows the results of this round-robin test. For Operator I, the average scratching coefficient of friction was 0.433, with a standard deviation of±0.010. For Operator II, the average scratching coefficient of friction was 0.434, with a standard deviation of ±0.010. For Operator III, the average scratching coefficient of friction was 0.433, with a standard deviation of ±0.005.

TABLE 4

Repeatability Data - Scratching Coefficient of Friction (Three Operators)

| Operator | Average | $S_r^A$ |
|---|---|---|
| I | 0.439 | ±0.010 |
| II | 0.434 | ±0.010 |
| III | 0.439 | ±0.005 |

What is claimed is:

1. A scratch testing device for scratch testing the surface of a material specimen, comprising:
    a scratching member;
    a lead screw, wherein said lead screw is rotatable with variable rotational speed;
    a guide rod;
    a carriage operable to move said scratching member, wherein said carriage is coupled to said lead screw, and wherein said carriage moves linearly when said lead screw rotates, and further wherein said guide rod guides linear motion of said carriage; and
    a load mechanism, wherein said load mechanism applies a load to said scratching member.

2. The device of claim 1, wherein the scratching member has a first end near the material specimen and a second end away from the material specimen;
    wherein a stylus is removably fixed to said first end; and
    wherein said stylus contacts the surface of the specimen when the load is applied to said scratching member.

3. The device of claim 1, further comprising a load sensor, wherein said load sensor measures the load applied to the scratching member.

4. The device of claim 1, wherein said load mechanism applies an increasing load to the scratching member.

5. The device of claim 1, wherein the load is applied substantially perpendicular to the surface of the material specimen.

6. The device of claim 1, further comprising a drive motor.

7. The device of claim 6, further comprising:
a scratch depth sensor;
a linear position sensor; and
a linear force sensor.

8. The device of claim 7, further comprising
a control center in communication with the scratch depth sensor, the linear position sensor, and the linear force sensor;
wherein said control center receives and stores a measured depth of a scratch; a measured location, direction, speed, acceleration, or combination thereof of the scratching member, and a measured tangential force acting on the scratching member; and
wherein said control center controls the drive motor and the load mechanism.

9. The device of claim 1, wherein the load mechanism is a pneumatic diaphragm.

10. The device of claim 1, wherein the load mechanism is a spring-loaded mechanism.

11. The device of claim 1, wherein the load mechanism is a dead-weight.

12. A method of scratch testing a material specimen, comprising:
(a) securing the material specimen to a testing surface;
(b) applying a load to a scratching member, wherein said load is applied by a load mechanism;
(c) positioning said scratching member at a start point;
(d) moving said scratching member across the surface of the material specimen from said start point to an end point by rotation of a lead screw, wherein said lead screw has variable rotational speed;
(e) guiding said scratching member across the surface with a guide rod; and
(f) analyzing the surface of the material specimen.

13. The method of claim 12, applying an increasing load to the scratching member while said scratching member is moving across the surface of the material specimen.

14. The method of claim 13, wherein the load mechanism is pneumatic.

15. The method of claim 13, wherein said load mechanism is a spring-loaded mechanism.

16. The method of claim 12, wherein a drive motor controls a location, direction, speed, acceleration or combination thereof of the scratching member.

17. The method of claim 16, further comprising defining a set of testing parameters.

18. The method of claim 17, wherein step (d) further comprises measuring a set of actual test data with a plurality of sensors.

19. The method of claim 18, wherein the plurality of sensors comprises:
a scratch depth sensor to measure the depth of a scratch in the surface of the material specimen;
a linear position sensor to measure a location, direction, speed, acceleration, or combination thereof of the scratching member; and
a linear force sensor to measure the tangential force acting on the scratching member.

20. The method of claim 18, further comprising comparing the set of testing parameters to the set of actual testing data, and controlling the drive motor and the load mechanism to achieve said set of testing parameters.

* * * * *